United States Patent
Chinsoga et al.

(10) Patent No.: US 11,525,543 B2
(45) Date of Patent: Dec. 13, 2022

(54) STORAGE METHOD FOR HYDROCHLOROFLUOROOLEFIN, AND STORAGE CONTAINER FOR HYDROCHLOROFLUOROOLEFIN

(71) Applicant: AGC Inc., Chiyoda-ku (JP)

(72) Inventors: Tamaki Chinsoga, Chiyoda-ku (JP); Masato Fukushima, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 371 days.

(21) Appl. No.: 16/835,565

(22) Filed: Mar. 31, 2020

(65) Prior Publication Data

US 2020/0224822 A1 Jul. 16, 2020

Related U.S. Application Data

(63) Continuation of application No. PCT/JP2018/037751, filed on Oct. 10, 2018.

(30) Foreign Application Priority Data

Oct. 20, 2017 (JP) .............................. JP2017-204017

(51) Int. Cl.
*F17C 1/00* (2006.01)
*C07C 21/18* (2006.01)
*F17C 5/02* (2006.01)
*C07C 21/185* (2006.01)

(52) U.S. Cl.
CPC ............ *F17C 1/005* (2013.01); *C07C 21/185* (2013.01); *F17C 5/02* (2013.01); *F17C 2221/038* (2013.01); *F17C 2270/01* (2013.01)

(58) Field of Classification Search
CPC ............ F16J 12/00; F17C 1/005; F17C 1/00; F17C 5/02; F17C 5/06; C07C 21/185; C07C 21/18; C07C 21/02
USPC ........................................... 220/581; 206/0.6
See application file for complete search history.

(56) References Cited

U.S. PATENT DOCUMENTS

| | | | |
|---|---|---|---|
| 2014/0077122 A1 | 3/2014 | Fukushima | |
| 2015/0051426 A1 | 2/2015 | Fukushima et al. | |
| 2016/0023034 A1* | 1/2016 | Elsheikh | C09K 3/00 516/8 |
| 2016/0123534 A1 | 5/2016 | Tsuzaki et al. | |
| 2016/0230059 A1 | 8/2016 | Takahashi et al. | |
| 2016/0230060 A1 | 8/2016 | Takahashi et al. | |
| 2016/0251282 A1* | 9/2016 | Bonnet | C07C 17/21 570/160 |
| 2016/0289148 A1 | 10/2016 | Fukushima et al. | |
| 2017/0058170 A1 | 3/2017 | Takahashi et al. | |
| 2017/0101567 A1 | 4/2017 | Fukushima | |
| 2017/0101568 A1 | 4/2017 | Fukushima | |
| 2017/0204029 A1 | 7/2017 | Fukushima et al. | |
| 2018/0016213 A1 | 1/2018 | Fukushima et al. | |
| 2018/0066170 A1* | 3/2018 | Tasaka | C09K 5/044 |

FOREIGN PATENT DOCUMENTS

| TL | WO 2013/161724 A1 | 10/2013 |
|---|---|---|
| WO | WO 2012/157763 A1 | 11/2012 |
| WO | WO 2015/008695 A1 | 1/2015 |
| WO | WO 2016/047297 A1 | 3/2016 |
| WO | WO 2016/047298 A1 | 3/2016 |

OTHER PUBLICATIONS

International Search Report dated Dec. 25, 2018 in PCT/JP2018/037751 filed Oct. 10, 2018, 2 pages.

* cited by examiner

*Primary Examiner* — Robert J Hicks

(74) *Attorney, Agent, or Firm* — Oblon, McClelland, Maier & Neustadt, L.L.P.

(57) ABSTRACT

To provide a method for safely and stably storing a hydrochlorofluoroolefin filled in a container for storage, transportation, etc. A method for storing a hydrochlorofluoroolefin in a sealed storage container, wherein the hydrochlorofluoroolefin is stored in such a state that a gas phase and a liquid phase coexist in the storage container, and the concentration of air in the gas phase in the storage container at a temperature of 25° C. is kept to be at most 3.0 vol %, and a method for storing a hydrochlorofluoroolefin in a sealed storage container, wherein the hydrochlorofluoroolefin is stored in such a state that a gas phase and a liquid phase coexist in the storage container, and the concentration of oxygen in the gas phase in the storage container at a temperature of 25° C. is kept to be at most 0.6 vol %.

18 Claims, No Drawings

STORAGE METHOD FOR HYDROCHLOROFLUOROOLEFIN, AND STORAGE CONTAINER FOR HYDROCHLOROFLUOROOLEFIN

This application is a continuation of PCT Application No. PCT/JP2018/037751, filed on Oct. 10, 2018, which is based upon and claims the benefit of priority from Japanese Patent Application No. 2017-204017 filed on Oct. 20, 2017. The contents of those applications are incorporated herein by reference in their entireties.

TECHNICAL FIELD

The present invention relates to a storage method and a storage container for a hydrochlorofluoroolefin, particularly a method for stably storing a hydrochlorofluoroolefin for storage, transportation, etc., and a container in which a hydrochlorofluoroolefin is stably stored.

BACKGROUND ART

In recent years, a hydrochlorofluoroolefin is expected as a new refrigerant, solvent, detergent, etc. which replaces chlorofluorocarbons, hydrochlorofluorocarbons and hydrofluorocarbons being greenhouse gases that destroy the ozone layer.

Such a hydrochlorofluoroolefin is stored or transported as filled in a sealed container under pressure at a temperature of at most room temperature, or as liquified and filled in a sealed container under pressure with cooling. The hydrochlorofluoroolefin thus filled in a sealed container is in a gas-liquid state having a gas phase and a liquid phase. And, the hydrochlorofluoroolefin in a gas-liquid state is desired to be stored stably without causing decomposition, oxidation or the like, in order to maintain the quality so as to be adapted to a refrigerant, a solvent, a detergent, etc., or to prevent deposition of impurities (solids) in the container.

A hydrofluoroolefin having an unsaturated double bond, like the hydrochlorofluoroolefin, is known to undergo a polymerization reaction if oxygen is present, since oxygen becomes a radical source. Accordingly, when a hydrofluoroolefin is stored, the acceptable oxygen content is determined by evaluating to what extent the hydrofluoroolefin is stable against self-polymerization in the presence of oxygen, and further considering the economical efficiency, e.g. the production cost (for example, Patent Document 1).

Further, with respect to use of the hydrochlorofluoroolefin, for example, as a refrigerant, a method has been known to stabilize the entire cooling system by assuming the presence of a refrigerant oil, and e.g. by adding a stabilizer to stabilize a refrigerant composition (for example, Patent Document 2). However, since the conditions are different from stabilization of the hydrochlorofluoroolefin in a container for storage or transportation, and therefore, it is difficult to apply such a method to storage of the hydrochlorofluoroolefin in a container. Further, in the method of adding a stabilizer, it is required to remove the stabilizer in application to a refrigerant, etc., whereby not only the load of the process is large, but also there may be a case where the stabilizer cannot be completely removed by a physical purification method such as distillation, such being undesirable from the viewpoint of quality control.

As described above, for a hydrochlorofluoroolefin, a technique regarding a storage method to maintain the quality to be adapted to various applications and for safe and stable storage and transportation, has not been established yet.

PRIOR ART DOCUMENTS

Patent Documents

Patent Document 1: WO2013/161724
Patent Document 2: WO2012/157763

DISCLOSURE OF INVENTION

Technical Problem

Under these circumstances, it is an object of the present invention to provide a method for safely and stably storing a hydrochlorofluoroolefin filled in a container for storage or transportation, and a container in which a hydrochlorofluoroolefin is stably stored.

Solution to Problem

The present invention provides a method for storing a hydrochlorofluoroolefin and a storage container for a hydrochlorofluoroolefin, having the following constitutions.

[1] A method for storing a hydrochlorofluoroolefin in a sealed storage container, wherein the hydrochlorofluoroolefin is stored in such a state that a gas phase and a liquid phase coexist in the storage container, and the concentration of air in the gas phase in the storage container at a temperature of 25° C. is kept to be at most 3.0 vol %.

[2] The method for storing a hydrochlorofluoroolefin according to [1], wherein the concentration of air is kept to be at least 1 vol ppm and at most 3.0 vol %.

[3] The method for storing a hydrochlorofluoroolefin according to [1] or [2], wherein the hydrochlorofluoroolefin is a $C_{2-5}$ hydrochlorofluoroolefin.

[4] The method for storing a hydrochlorofluoroolefin according to any one of [1] to [3], wherein the hydrochlorofluoroolefin contains 1-chloro-2,3,3,3-tetrafluoropropene.

[5] The method for storing a hydrochlorofluoroolefin according to any one of [1] to [4], wherein air in an unfilled storage container is removed, then, a liquid-state hydrochlorofluoroolefin is filled and sealed, and the hydrochlorofluoroolefin is stored in the sealed storage container.

[6] A storage container for a hydrochlorofluoroolefin, which is a sealed storage container in which the hydrochlorofluoroolefin is filled in such a state that a gas phase and a liquid phase coexist, and in which the concentration of air in the gas phase at a temperature of 25° C. is at most 3.0 vol %.

[7] The storage container for a hydrochlorofluoroolefin according to [6], wherein the concentration of air is at least 1 vol ppm and at most 3.0 vol %.

[8] The storage container for a hydrochlorofluoroolefin according to [6] or [7], wherein the hydrochlorofluoroolefin is a $C_{2-5}$ hydrochlorofluoroolefin.

[9] The storage container for a hydrochlorofluoroolefin according to any one of [6] to [8], wherein the hydrochlorofluoroolefin contains 1-chloro-2,3,3,3-tetrafluoropropene.

[10] A method for storing a hydrochlorofluoroolefin in a sealed storage container, wherein the hydrochlorofluoroolefin is stored in such a state that a gas phase and a liquid phase coexist in the storage container, and the concentration of oxygen in the gas phase in the storage container at a temperature of 25° C. is kept to be at most 0.6 vol %.

[11] The method for storing a hydrochlorofluoroolefin according to [10], wherein the concentration of oxygen is kept to be at least 0.2 vol ppm and at most 0.6 vol %.

[12] The method for storing a hydrochlorofluoroolefin according to [10] or [11], wherein the hydrochlorofluoroolefin is a $C_{2-5}$ hydrochlorofluoroolefin.

[13] The method for storing a hydrochlorofluoroolefin according to any one of [10] to [12], wherein the hydrochlorofluoroolefin contains 1-chloro-2,3,3,3-tetrafluoropropene.

[14] The method for storing a hydrochlorofluoroolefin according to any one of [10] to [13], wherein air in an unfilled storage container is removed, then, a liquid-state hydrochlorofluoroolefin is filled and sealed, and the hydrochlorofluoroolefin is stored in the sealed storage container.

[15] A storage container for a hydrochlorofluoroolefin, which is a sealed storage container in which the hydrochlorofluoroolefin is filled in such a state that a gas phase and a liquid phase coexist, and in which the concentration of oxygen in the gas phase at a temperature of 25° C. is at most 0.6 vol %.

[16] The storage container for a hydrochlorofluoroolefin according to [15], wherein the concentration of oxygen is at least 0.2 vol ppm and at most 0.6 vol %.

[17] The storage container for a hydrochlorofluoroolefin according to [15] or [16], wherein the hydrochlorofluoroolefin is a $C_{2-5}$ hydrochlorofluoroolefin.

[18] The storage container for a hydrochlorofluoroolefin according to any one of [15] to [17], wherein the hydrochlorofluoroolefin contains 1-chloro-2,3,3,3-tetrafluoropropene.

Advantageous Effects of Invention

According to the method for storing a hydrochlorofluoroolefin and the storage container for a hydrochlorofluoroolefin of the present invention, decomposition, oxidation or the like of a hydrochlorofluoroolefin is suppressed, whereby it is possible to maintain the hydrochlorofluoroolefin with high purity and high quality.

DESCRIPTION OF EMBODIMENTS

Now, the present invention will be described in detail below.

In this specification, abbreviated names of halogenated hydrocarbon compounds are described in brackets after the compound names, and the abbreviated names are employed instead of the compound names as the case requires. Further, with respect to a compound having cis-trans isomers, (E) before the compound name or after the abbreviated name means an E-form (trans form), and (Z) means a Z-form (cis form). A compound or an abbreviated name not denoted by (E) or (Z) means an E-form, a Z-form and a mixture of an E-form and a Z-form.

In this specification, unless otherwise specified, the concentration of air in a gas phase of the hydrochlorofluoroolefin is the concentration of air at a gas temperature of 25° C. In this specification, air comprises 20 vol % of oxygen and 80 vol % of nitrogen to the total volume of air.

According to a first embodiment of the present invention, provided is a method for storing a hydrochlorofluoroolefin in a sealed storage container, wherein the hydrochlorofluoroolefin is stored in such a state that a gas phase and a liquid phase coexist in the storage container, and the concentration of air in the gas phase in the storage container at a temperature of 25° C. is kept to be at most 3.0 vol %. In the sealed container, the hydrochlorofluoroolefin is kept in a gas-liquid coexistence state, and therefore, the pressure of the hydrochlorofluoroolefin in the storage container is a saturated vapor pressure of the hydrochlorofluoroolefin. The concentration of air may be regarded as a proportion of air contained in the gas phase in the storage container containing the hydrochlorofluoroolefin and air.

A part of the hydrochlorofluoroolefin in a storage container is taken out, and thereafter, the rest of the hydrochlorofluoroolefin will be continuously stored in the storage container in not a few cases. In such a case, the volume of the gas phase in the storage container increases, but the concentration of air in the gas phase having the volume increased will be kept to be at most 3.0 vol %. The concentration of air in the gas phase is usually in an equilibrium state with the concentration of air in the hydrochlorofluoroolefin in the liquid phase, and therefore, it is considered that unless air enters into the storage container when the part of the hydrochlorofluoroolefin is taken out, the concentration of air in the gas phase would not substantially increase.

According to a second embodiment of the present invention, provided is a storage container for a hydrochlorofluoroolefin, which is a sealed storage container in which the hydrochlorofluoroolefin is filled in such a state that a gas phase and a liquid phase coexist, and in which the concentration of air in the gas phase at a temperature of 25° C. is at most 3.0 vol %.

According to a third embodiment of the present invention, provided is a method for storing a hydrochlorofluoroolefin in a sealed storage container, wherein the hydrochlorofluoroolefin is stored in such a state that a gas phase and a liquid phase coexist in the storage container, and the concentration of oxygen in the gas phase in the storage container at a temperature of 25° C. is kept to be at most 0.6 vol %.

According to a fourth embodiment of the present invention, provided is a storage container for a hydrochlorofluoroolefin, which is a sealed storage container in which the hydrochlorofluoroolefin is filled in such a state that a gas phase and a liquid phase coexist, and in which the concentration of oxygen in the gas phase at a temperature of 25° C. is at most 0.6 vol %.

In the first to fourth embodiments of the present invention, as the hydrochlorofluoroolefin, specifically, a 02-10 hydrochlorofluoroolefin may be mentioned. The hydrochlorofluoroolefin to which the present invention is suitably applicable, has from 2 to 8 carbon atoms, more preferably from 2 to 5 carbon atoms.

The $C_2$ hydrochlorofluoroolefin may be 1-chloro-2,2-difluoroethylene (HCFO-1122), 1,2-dichlorofluoroethylene (HCFO-1121) or 1-chloro-2-fluoroethylene (HCFO-1131).

The $C_3$ hydrochlorofluoroolefin may, for example, be 1-chloro-2,3,3,3-tetrafluoropropene (HCFO-1224yd), 2-chloro-1,3,3,3-tetrafluoropropene (HCFO-1224xe), 1-chloro-1,3,3,3-tetrafluoropropene (HCFO-1224zb), 2-chloro-3,3,3-trifluoropropene (HCFO-1233xf), 1-chloro-2,3,3-trifluoropropene (HCFO-1233yd), 1-chloro-3,3,3-trifluoropropene (HCFO-1233zd), 1-chloro-1,3,3-trifluoropropene (HCFO-1233zb), 2-chloro-1,3,3-trifluoropropene (HCFO-1233xe), 2-chloro-1,1,3-trifluoropropene (HCFO-1233xc), 3-chloro-1,2,3-trifluoropropene (HCFO-1233ye), 3-chloro-1,1,2-trifluoropropene (HCFO-1233yc), 1,2-dichloro-3,3,3-trifluoropropene (HCFO-1223xd), 1,3-dichloro-2,3,3-trifluoropropene (HCFO-1223yd), 2,3-dichloro-3,3-difluoropropene (HCFO-1232xf), 1,2,3-trichloro-3,3-difluoropropene (HCFO-1222xd) or 2,3,3-trichloro-3-fluoropropene (HCFO-1231xf).

The $C_5$ hydrochlorofluoroolefin may, for example, be 1-chloro-2,3,3,4,4,5,5-heptafluoro-1-pentene (HCFO-1437dycc).

In the first to fourth embodiments of the present invention, the hydrochlorofluoroolefin may be stored as a mixture of a plural types of hydrochlorofluoroolefins, or may be stored alone.

The storage container for a hydrochlorofluoroolefin does not require any special structure or material, so long as it is a sealed container capable of enclosing a gas-liquid mixture under internal pressure, and it may have a wide range of forms and functions. For example, a storage tank being a fixed storage container, or a pressure resistant container such as a filling cylinder or a secondary filling cylinder (service can) to be used for transportation, may be mentioned. As the material for the storage container, it is possible to use, for example, a metal composed mainly of one material or two or more materials selected from carbon steel, manganese steel, chromium-molybdenum steel, other low alloy steel, stainless steel, aluminum alloy, copper, iron, aluminum, nickel, titanium, metal silicon, silicon steel, tin, magnesium and a zinc.

According to the first and second embodiments of the present invention, the concentration of air in the gas phase in the storage container is at most 3.0 vol %. When the concentration of air in the gas phase is at most 3.0 vol %, decomposition, oxidation or the like of the hydrochlorofluoroolefin in a liquid phase and in a gas phase can be sufficiently prevented, and the quality can be maintained.

According to the third and fourth embodiments of the present invention, the concentration of oxygen in the gas phase in the storage container is at most 0.6 vol %. When the concentration of oxygen in the gas phase is at most 0.6 vol %, decomposition, oxidation or the like of the hydrochlorofluoroolefin in a liquid phase and in a gas phase can be sufficiently prevented, and the quality can be maintained.

The present inventors have found that a hydrofluoroolefin having an unsaturated double bond like the hydrochlorofluoroolefin undergoes a polymerization reaction in the presence of a small amount of oxygen, whereas the hydrochlorofluoroolefin does not undergo a polymerization reaction even in the presence of oxygen to such an extent that a hydrofluoroolefin undergoes a polymerization reaction.

And, the present inventors have conducted extensive studies on the basis of discoveries such that for storage of the hydrochlorofluoroolefin, the amount of presence of oxygen or air containing oxygen can be defined from the viewpoint different from that of the hydrofluoroolefin, and as a result, found that the quality of the hydrochlorofluoroolefin can be maintained when the concentration of air in the gas phase is at most 3.0 vol %, or the concentration of oxygen is at most 0.60 vol %. To maintain higher quality of the hydrochlorofluoroolefin in a longer period of time, it is preferred that the concentration of air in the gas phase is at most 1.7 vol % and the concentration of oxygen is at most 0.34 vol %, and it is more preferred that the concentration of air is at most 0.7 vol % and the concentration of oxygen is at most 0.14 vol %.

As described above, in the first and second embodiments of the present invention, to define the concentration of air in the gas phase to be at most a specific value is synonymous with defining the concentration of oxygen to be at most one fifth of the specific value of the air concentration. In the present invention, when the hydrochlorofluoroolefin is stored in a storage container, usually, the amount of air or oxygen included in the storage container is defined as above, whereby the amount of oxygen which accelerates decomposition, oxidation or the like of the hydrochlorofluoroolefin is defined.

From the viewpoint of operation property at the time of filling in a storage container, the concentration of air in the gas phase is preferably from 1.8 to 3.0 vol %, and the concentration of oxygen is preferably from 0.36 to 0.6 vol %.

Further, the concentration of air in the gas phase is at least 1 vol ppm, whereby the production cost, etc. can be suppressed. In view of the production cost, the concentration of air in the gas phase is more preferably at least 3 vol ppm, further preferably at least 5 vol ppm, particularly preferably at least 7 vol ppm. The concentration of oxygen in the gas phase is preferably at least 0.2 vol ppm, whereby the production cost, etc. can be suppressed. In view of the production cost, the concentration of air in the gas phase is more preferably at least 0.6 vol ppm, further preferably at least 1 vol ppm, particularly preferably at least 1.4 vol ppm.

In the first and second embodiments of the present invention, the concentration of air in the gas phase is, from the above-described viewpoint, preferably at least 1 vol ppm and at most 3.0 vol %, more preferably at least 3 vol ppm and at most 1.7 vol %, further preferably at least 3 vol ppm and at most 0.7 vol %.

In the third and fourth embodiments of the present invention, the concentration of oxygen in the gas phase is, from the above-described viewpoint, preferably at least 0.2 vol ppm and at most 0.6 vol %, more preferably at least 0.6 vol ppm and at most 0.34 vol %, further preferably at least 0.6 vol ppm and at most 0.14 vol %.

The hydrochlorofluoroolefin to which the first to fourth embodiments of the present invention are more suitably applicable, among the above hydrochlorofluoroolefins, may be the $C_3$ hydrochlorofluoropropene, preferably at least one member selected from a monochlorotetrafluoropropene and a monochlorotrifluoropropene, particularly preferably HCFO-1224yd (hereinafter sometimes referred to as "1224yd").

1224yd ($CF_3$—CF=CHCl) has high stability among hydrochlorofluoroolefins. Therefore, when the first and second embodiments of the present invention are applied to 1224yd, the lower limit of the concentration of air in the gas phase may be set, for example, at 10 vol ppm, more preferably 15 vol ppm. When the third and fourth embodiments of the present invention are applied to 1224yd, the lower limit of the concentration of oxygen in the gas phase may be set, for example, at 2 vol ppm, more preferably 3 vol ppm.

1224yd has cis-trans isomers 1224yd(Z) and 1224yd(E), and 1224yd(Z) has high chemical stability as compared with 1224yd(E). 1224yd has, from the viewpoint of chemical stability, a proportion of 1224yd(Z) to the total amount of 1224yd of preferably from 30 to 100 mass %, more preferably from 50 to 100 mass %, further preferably from 80 to 100 mass %, particularly preferably from 99 to 100 mass %. 1224yd particularly preferably consists solely of 1224yd(Z). When the first and second embodiments of the present invention are applied to 1224yd(Z), the lower limit of the concentration of air in the gas phase may be set, for example, at 20 vol ppm, more preferably 25 vol ppm, further preferably 50 vol ppm, most preferably 80 vol ppm.

When the third and fourth embodiments of the present invention are applied to 1224yd(Z), the lower limit of the concentration of oxygen in the gas phase may be set, for example, at 4 vol ppm, more preferably 5 vol ppm, further preferably 10 vol ppm, most preferably 16 vol ppm.

In the first to fourth embodiments of the present invention, in the storage container, in addition to the hydrochlorofluoroolefin and air or oxygen, trace components may be present within a range not to impair the effects of the present invention. The trace components may be by-products formed in production of the hydrochlorofluoroolefin, unreacted raw materials, and various compounds used for purification. In such a case, the concentration of air or oxygen in the gas phase is the concentration of air or oxygen to a gas phase portion in the storage container in which the hydrochlorofluoroolefin, the trace components and air are contained.

The content of such trace components is, for example, to the total amount of the hydrochlorofluoroolefin to be stored and the trace components, preferably less than 1.5 mass % in total, more preferably at most 1.0 mass %. However, in the first to fourth embodiments of the present invention, from the viewpoint of the production cost, the lower limit of the content of the trace components may be preferably 4 mass ppm, more preferably 50 mass ppm, further preferably 100 mass ppm. So long as the content of the trace components is at most the upper limit value, even if it is at least the above lower limit value, in the first to fourth embodiments of the present invention, the concentration of air or oxygen in the gas phase is sufficiently suppressed, and therefore the effects of the present invention can be achieved.

In the first to fourth embodiments of the present invention, in a case where 1224yd is stored in the storage container, such trace components may be at least one member selected from 1,3-dichloro-1,1,2,2,3-pentafluoropropane (CClF$_2$—CF$_2$—CHClF, HCFC-225cb), 1,1,1,2-tetrafluoropropane (CF$_3$—CHF—CH$_3$, HFC-254eb), 1,1-dichloro-2,3,3,3-tetrafluoropropene (CF$_3$—CF=CCl$_2$, CFO-1214ya), (Z)-2-chloro-1,3,3,3-tetrafluoropropene ((Z)-CF$_3$—CCl=CHF, HCFO-1224xe(Z)), (E)-2-chloro-1,3,3,3-tetrafluoropropene ((E)-CF$_3$—CCl=CHF, HCFO-1224xe(E)), 2,3,3,3-tetrafluoropropene (CF$_3$—CF=CH$_2$, HFO-1234yf), (Z)-1,3,3,3-tetrafluoropropene ((Z)—CF$_3$—CH=CHF, HFO-1234ze (Z)), (E)-1,3,3,3-tetrafluoropropene ((E)-CF$_3$—CH=CHF, HFO-1234ze(E)), 1-chloro-3,3,3-trifluoro-1-propyne (CF$_3$—C≡CCl), fluorinated hydrocarbon represented by C$_4$H$_4$F$_4$, 2-chloro-1,1,1,2-tetrafluoropropane (HCFC-244bb), 1,1,1,3,3-pentafluoropropane (HFC-245fa), 2-chloro-1,1,3,3-pentafluoro-1-propene (CFO-1215xc), 3,3-dichloro-1,1,1,2,2-pentafluoropropane (HCFC-225ca), 1,1,1,2,2,3,3-heptafluoropropane (FC-227ca), methanol, ethanol, acetone, chloroform and hexane.

Further, the above trace components may sometimes have, depending upon the type of the compound, a specific function when contained in an appropriate amount of less than 1.5 mass % to the total amount of 1224yd and the trace components. For example, 1-chloro-3,3,3-trifluoro-1-propyne is a compound which increases stability of 1224yd when contained in an amount of less than 1.5 mass % to the total amount of 1224yd and the trace components. From the viewpoint of stability of 1224yd, 1-chloro-3,3,3-trifluoro-1-propyne is contained in an amount of from 0.0001 to 0.1 mass %, more preferably from 0.0001 to 0.001 mass % to the total amount of 1224yd and the trace components.

Further, for example, HCFC-244bb is a compound which increases stability of 1224yd when contained in an amount of less than 1.5 mass % to the total amount of 1224yd and the trace components. From the viewpoint of stability of 1224yd, HCFC-244bb is contained preferably in an amount of from 0.001 to 0.5 mass %, more preferably from 0.01 to 0.1 mass % to the total amount of 1224yd and the trace components.

Further, the trace components may contain a hydrofluoroolefin, for example, in the case of 1224yd, HF-1234yf, HFO-1234ze(E), HFO-1234ze(Z) and fluorinated hydrocarbon represented by C$_4$H$_4$F$_4$. However, the hydrofluoroolefin may be polymerized in the presence of a very small amount of oxygen to form a solid polymerized product in the container, and accordingly the content of the hydrofluoroolefin to the total amount of the hydrochlorofluoroolefin to be stored and the trace components is preferably at most 5,000 mass ppm in total, more preferably at most 2,000 mass ppm. Considering the production cost, the lower limit of the content of the hydrofluoroolefin to the total amount of the hydrochlorofluoroolefin to be stored and the trace components is preferably 50 mass ppm, more preferably 100 mass ppm.

In a case where 1224yd is stored in the storage container, if the above trace components are present, it is preferred that the amount of air in the storage container is from 5 vol ppm to 1.5 vol %, or the amount of oxygen is from 1 vol ppm to 0.3 vol %, with a view to further improving the stability of 1224yd, and it is more preferred that the amount of air is from 7 vol ppm to 1.0 vol %, or the amount of oxygen is from 1.4 vol ppm to 0.2 vol %.

Further, according to the first to fourth embodiments of the present invention, it is preferred that no water is contained in the storage container. The upper limit of the amount of water which can be contained without impairing the effects of the present invention is preferably 20 mass ppm, more preferably 15 mass ppm, further preferably 10 mass ppm, particularly preferably 5 mass ppm to the total amount of the desired hydrochlorofluoroolefin and the trace components. Considering the production cost, the lower limit of the amount of water is preferably 0.1 mass ppm, more preferably 1 mass ppm, to the total amount of the hydrochlorofluoroolefin to be stored and the trace components.

In order that the amount of water in the storage container is within the above range, before the hydrochlorofluoroolefin is filled in the storage container, the amount of water in the hydrochlorofluoroolefin can be reduced by a known method such as bringing the hydrochlorofluoroolefin into contact with a solid adsorbent such as molecular sieves. The amount of water in the hydrochlorofluoroolefin may be measured by Karl Fischer coulometric titration method.

In the first to fourth embodiments of the present invention, adjustment of the concentration of air or oxygen in the gas phase may be conducted by pressurizing the hydrochlorofluoroolefin to form a liquid and injecting this liquid into a sealed container having the concentration of air reduced to at most 3.0 vol % at a temperature of 25° C. or the concentration of oxygen reduced to at most 0.6 vol % at a temperature of 25° C. by preliminary vacuum deaeration of air. When the liquid of the hydrochlorofluoroolefin is injected into the container, the space in the container will be quickly saturated with the vapor from the liquid. And, in the gas phase gas filled with saturated vapor of the hydrochlorofluoroolefin, the concentration of air becomes to be at most 3.0 vol % (temperature: 25° C.) or the concentration of oxygen becomes to be at most 0.6 vol % (temperature: 25° C.). The concentrations of air and oxygen in the gas phase may be measured by gas chromatography.

In the first to fourth embodiments of the present invention, the acid content of the hydrochlorofluoroolefin in the storage container after left to stand in a constant temperature state of 125° C. for 5 days is preferably less than 30 mass ppm, more preferably less than 10 mass ppm, further preferably less than 1 mass ppm to the total amount of the hydrochlorofluoroolefin. The acid content in the storage container is obtained by the measurement method disclosed in the after-described Examples. In a case where the trace components are present in the storage container, the acid content to the total amount of the hydrochlorofluoroolefin and the trace components is preferably less than 30 mass ppm.

According to such a storage method for the hydrochlorofluoroolefin of the present invention, the hydrochlorofluoroolefin filled in a gas-liquid state in the sealed container will not undergo decomposition, oxidation or the like, whereby it is possible to maintain the purity and the high quality as a refrigerant or the like, of the hydrochlorofluoroolefin. Further, in a preferred embodiment such that the lower limit of the concentration of air in the gas phase is 1 vol ppm or the lower limit of the concentration of oxygen is 0.2 vol ppm, the hydrochlorofluoroolefin can be stored at a low cost. Further, by defining the content of the hydrofluoroolefin as the trace components, no solid polymerized product will be formed in the sealed container, whereby clogging of a valve, etc. or contamination to the refrigerating system, is less likely to occur.

Evaluation of the storage method of the present invention may be conducted, for example, in such a manner that the hydrochlorofluoroolefin is injected together with a predetermined amount of air or oxygen into a sealed container to achieve a gas-liquid coexistence state, and the entirety is heated to a predetermined temperature and held in a constant temperature state for a predetermined time, whereupon reaction products in the liquid phase of the hydrochlorofluoroolefin will be identified and analyzed. This evaluation corresponds to an accelerated test in which a thermal load is applied. The heating temperature may be set in a range of from −70 to 300° C. which is a set temperature range of the constant temperature vessel. Further, the heat treatment time may be optionally set. The identification and analysis of the reaction products may be carried out, for example, by the methods described in Examples given hereinafter.

EXAMPLES

Now, the present invention will be described in detail with reference to Examples, but the present invention is by no means limited to the following Examples. Ex. 1 to 8 are Examples of the present invention, and Ex. 9 and 10 are Comparative Examples. Ex. 11 to 13 are Reference Examples using a hydrofluoroolefin.

Ex. 1 to 10

In a SUS316 pressure-resistant container having an internal volume of 200 cc (maximum operating temperature: 300° C., maximum working pressure: 20 MPa), a tube made of Pyrex (registered trademark) having the weight preliminarily measured, was inserted. The pressure-resistant container was sealed, and the container was evacuated of air. The tube was inserted to confirm the presence or absence of formation of a polymer in the pressure-resistant test container. Then, a predetermined amount of air was introduced into the pressure-resistant container, and 50 g of a 1224yd(Z) composition containing liquified 1224yd(Z) and trace components was filled. The gas phase in the pressure-resistant container was collected, and the concentration of air was measured by gas chromatography, whereupon a value shown in Table 1 was obtained. The temperature in the pressure-resistant container when the sample was collected was 25° C. The concentration of oxygen determined from the concentration of air is shown in Table 1.

The trace components in the 1224yd(Z) composition were HFC-254eb, HFO-1234ze(Z), fluorinated hydrocarbon represented by $C_4H_4F_4$, HCFC-244bb, HFC-245fa, CFO-1215xc, FC-227ca, HCFO-1224xe, HFO-1224yd(E), 1-chloro-3,3,3-trifluoro-1-propyne, HFO-1234yf and methanol, and their total content was 0.52 mass % to the total amount of 1224yd(Z) and the trace components. Further, the content of water was 20 mass ppm to the total amount of 1224yd(Z) and the trace components.

Then, the pressure-resistant container in which the 1224yd(Z) composition together with air at a predetermined concentration was filled, was placed in a hot air circulating constant temperature vessel and left to stand in a constant temperature state of 125° C. for 5 days.

Upon expiration of the 5 days, the pressure-resistant container was taken out from the constant temperature vessel, and the acid content in the 1224yd(Z) composition was analyzed as follows.

(Measurement of Acid Content)

The pressure-resistant container after the above test was left at rest until the temperature reached room temperature. To the pressure-resistant container at room temperature, a set of four absorption bottles each having 100 ml of pure water put, connected by a conductor tube in series, was connected, and the valve of the pressure-resistant container was gradually opened to introduce the 1224yd(Z) composition into water in the absorption bottles so that the acid content contained in the 1224yd(Z) composition was extracted.

The water in the first and second absorption bottles after extraction was titrated by a 1/100N-NaOH alkali standard solution with a drop of an indicator (BTB: bromothymol blue). Further, the water in the third and fourth absorption bottles were similarly titrated as a measurement blank. From such measured value and the measurement blank value, the concentration of the acid content contained in the 1224yd(Z) composition after the test was obtained as the HCl concentration. The results are shown in Table 1. In Table 1, ⊚ represents an acid content concentration of less than 1 mass ppm, ○ an acid content concentration of at least 1 mass ppm and less than 10 mass ppm, Δ an acid content concentration of at least 10 mass ppm and less than 30 mass ppm, and x an acid content concentration of at least 30 mass ppm.

Further, while the presence or absence of formation of a solid substance in the tube was visually examined, and the amount of the solid substance formed was examined by a mass change of the tube between before and after the test. The results are shown in Table 1. In Table 1, ○ represents an amount of the solid substance formed of at most 10 mg, and x an amount of the solid substance formed of more than 10 mg.

Ex. 11 to 13

For comparison with the hydrochlorofluoroolefin (HCFO), the following three types of hydrofluoroolefins (HFO) were filled in a pressure-resistant container so that the air concentration and the oxygen concentration in the gas phase were the same as in Ex. 3, and the same evaluations as above were conducted. The results are shown in Table 1.

HFO-1234yf having a purity of at least 99.5 mass % was used in Ex. 11, HFO-1234ze(E) having a purity of at least 99.5 mass % in Ex. 12, and trifluoroethylene (HFO-1123) having a purity of at least 99.5 mass % in Ex. 13.

TABLE 1

| Ex. | Type | Sample | Concentration in gas phase (vol %) Air | Concentration in gas phase (vol %) Oxygen | Acid content concentration Evaluation | Amount of solid substance formed Evaluation |
|---|---|---|---|---|---|---|
| Ex. 1 | HCFO | 1224yd(Z) composition | 0.01 | 0.002 | ⊚ | ○ |
| Ex. 2 | | | 0.1 | 0.02 | ⊚ | ○ |
| Ex. 3 | | | 0.3 | 0.06 | ⊚ | ○ |
| Ex. 4 | | | 0.8 | 0.2 | ○ | ○ |
| Ex. 5 | | | 1.3 | 0.26 | ○ | ○ |
| Ex. 6 | | | 1.8 | 0.36 | Δ | ○ |
| Ex. 7 | | | 2.1 | 0.42 | Δ | ○ |
| Ex. 8 | | | 2.5 | 0.50 | Δ | ○ |
| Ex. 9 | | | 3.1 | 0.62 | X | ○ |
| Ex. 10 | | | 4 | 0.8 | X | ○ |
| Ex. 11 | HFO | 1234yf | 0.3 | 0.06 | X | X |
| Ex. 12 | | 1234ze(E) | 0.3 | 0.06 | X | X |
| Ex. 13 | | 1123 | 0.3 | 0.06 | X | X |

It is found from Table 1 that the method of the present invention is effective as a stable storage method to store a hydrochlorofluoroolefin, which does not bring about decomposition and oxidation over a long period of time.

INDUSTRIAL APPLICABILITY

According to the storage method and the storage container of the present invention, the hydrochlorofluoroolefin does not undergo decomposition, oxidation or the like, whereby they can be useful for storage, transportation, etc. while high quality of the hydrochlorofluoroolefin is maintained.

What is claimed is:

1. A method for storing a hydrochlorofluoroolefin in a sealed storage container, wherein the hydrochlorofluoroolefin is stored in such a state that a gas phase and a liquid phase coexist in the storage container, and the concentration of air in the gas phase in the storage container at a temperature of 25° C. is kept to be at most 3.0 vol %.

2. The method for storing a hydrochlorofluoroolefin according to claim 1, wherein the concentration of air is kept to be at least 1 vol ppm and at most 3.0 vol %.

3. The method for storing a hydrochlorofluoroolefin according to claim 1, wherein the hydrochlorofluoroolefin is a $C_{2-5}$ hydrochlorofluoroolefin.

4. The method for storing a hydrochlorofluoroolefin according to claim 1, wherein the hydrochlorofluoroolefin contains 1-chloro-2,3,3,3-tetrafluoropropene.

5. The method for storing a hydrochlorofluoroolefin according to claim 1, wherein air in an unfilled storage container is removed, then, a liquid-state hydrochlorofluoroolefin is filled and sealed, and the hydrochlorofluoroolefin is stored in the sealed storage container.

6. A storage container for a hydrochlorofluoroolefin, which is a sealed storage container in which the hydrochlorofluoroolefin is filled in such a state that a gas phase and a liquid phase coexist, and in which the concentration of air in the gas phase at a temperature of 25° C. is at most 3.0 vol %.

7. The storage container for a hydrochlorofluoroolefin according to claim 6, wherein the concentration of air is at least 1 vol ppm and at most 3.0 vol %.

8. The storage container for a hydrochlorofluoroolefin according to claim 6, wherein the hydrochlorofluoroolefin is a $C_{2-5}$ hydrochlorofluoroolefin.

9. The storage container for a hydrochlorofluoroolefin according to claim 6, wherein the hydrochlorofluoroolefin contains 1-chloro-2,3,3,3-tetrafluoropropene.

10. A method for storing a hydrochlorofluoroolefin in a sealed storage container, wherein the hydrochlorofluoroolefin is stored in such a state that a gas phase and a liquid phase coexist in the storage container, and the concentration of oxygen in the gas phase in the storage container at a temperature of 25° C. is kept to be at most 0.6 vol %.

11. The method for storing a hydrochlorofluoroolefin according to claim 10, wherein the concentration of oxygen is kept to be at least 0.2 vol ppm and at most 0.6 vol %.

12. The method for storing a hydrochlorofluoroolefin according to claim 10, wherein the hydrochlorofluoroolefin is a $C_{2-5}$ hydrochlorofluoroolefin.

13. The method for storing a hydrochlorofluoroolefin according to claim 10, wherein the hydrochlorofluoroolefin contains 1-chloro-2,3,3,3-tetrafluoropropene.

14. The method for storing a hydrochlorofluoroolefin according to claim 10, wherein air in an unfilled storage container is removed, then, a liquid-state hydrochlorofluoroolefin is filled and sealed, and the hydrochlorofluoroolefin is stored in the sealed storage container.

15. A storage container for a hydrochlorofluoroolefin, which is a sealed storage container in which the hydrochlorofluoroolefin is filled in such a state that a gas phase and a liquid phase coexist, and in which the concentration of oxygen in the gas phase at a temperature of 25° C. is at most 0.6 vol %.

16. The storage container for a hydrochlorofluoroolefin according to claim 15, wherein the concentration of oxygen is at least 0.2 vol ppm and at most 0.6 vol %.

17. The storage container for a hydrochlorofluoroolefin according to claim 15, wherein the hydrochlorofluoroolefin is a $C_{2-5}$ hydrochlorofluoroolefin.

18. The storage container for a hydrochlorofluoroolefin according to claim 15, wherein the hydrochlorofluoroolefin contains 1-chloro-2,3,3,3-tetrafluoropropene.

* * * * *